United States Patent [19]

Mahood

[11] Patent Number: 5,464,889
[45] Date of Patent: Nov. 7, 1995

[54] PHOSPHITE ANTIOXIDANTS

[75] Inventor: James A. Mahood, Parkersburg, W. Va.

[73] Assignee: General Electric Company, Pittsfield, Mass.

[21] Appl. No.: 285,585

[22] Filed: Aug. 3, 1994

Related U.S. Application Data

[63] Continuation of Ser. No. 96,113, Jul. 22, 1993, abandoned.

[51] Int. Cl.$^6$ ............................ C08K 5/527; C07F 9/6574
[52] U.S. Cl. .............................. 524/119; 524/117; 558/78; 558/85
[58] Field of Search ....................... 558/78, 85; 524/117, 524/119

[56] References Cited

U.S. PATENT DOCUMENTS

| | | |
|---|---|---|
| 3,039,993 | 6/1992 | Friedman . |
| 3,056,823 | 10/1962 | Hecheubleikner et al. . |
| 3,133,043 | 5/1964 | Rosenfelder et al. ................... 524/119 |
| 3,149,181 | 9/1964 | Warren ..................................... 524/119 |
| 3,264,247 | 8/1966 | Friedman . |
| 3,281,381 | 10/1966 | Hecheubleikner et al. . |
| 3,305,520 | 2/1967 | Fritz et al. ............................... 524/151 |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall et al. . |
| 3,509,091 | 4/1970 | Cleveland et al. . |
| 3,558,554 | 1/1971 | Kuriyama et al. ...................... 524/151 |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Gattag . |
| 4,086,304 | 4/1978 | Hutton et al. . |
| 4,405,739 | 9/1983 | Kinson . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,956,406 | 9/1990 | Myers et al. . |
| 4,957,954 | 9/1990 | Iizuka et al. . |

*Primary Examiner*—Veronica P. Hoke

[57] ABSTRACT

Neoalkyl phosphite provided which exhibit improved levels of stability. The phosphites are hindered and are useful in stabilizing thermoplastic compositions.

6 Claims, No Drawings

PHOSPHITE ANTIOXIDANTS

This is a continuation of application Ser. No. 08/096,113 filed on Jul. 22, 1993, now abandoned.

BACKGROUND OF THE INVENTION

1. Field of the Invention

The present invention relates to phosphites, and more particularly, relates to neo-alkyl phosphites, the preparation thereof, and polymer compositions stabilized therein.

2. Description of the Related Art

Organic phosphites are known thermal oxidative stabilizing agents for polymers and other organic materials. Such phosphites however typically suffer from one or more of the following problems resulting from structural deficiencies: (a) they degrade to alcohols which undergo $H_2O$ (water) generation through beta-elimination of a hydrogen with an —OH group, and it is believed that this $H_2O$ generation can lead to further degradation of the phosphite; (b) they experience hydrolytic instability upon exposure to moisture which attacks the bond between the oxygen atoms and the phosphorus atom (O—P bonds); and (c) they degrade into alcohol degradation products which have boiling points of less than 250° C. which volatilize out of phosphite stabilized polymeric compositions under normal polymer processing conditions, for example degradation products such as low molecular weight diols such as 1,3 propane diol (BP 213° C.), 2,2 dimethyl-1,3 propane diol (BP 206° C.), 2,2 diethyl-1,3 propane diol (BP 240° C.), and 2 methyl, 2 propyl-1,3 propane diol (BP 234° C.). Finally, in processes for making organic phosphites it is desirable to be able to make the phosphite from a direct reaction between alcohols and $PCl_3$ but if a beta-hydrogen is present in the alcohol, then undesirable alkylchlorides will most likely form.

Neo-alkyl phosphites derived from a neoglycol with $PCl_3$ are known, see Dever, et al., U.S. Pat. No. 3,714,302, which is incorporated herein by reference. While these neo-alkyl phosphites have no β-hydrogens, they lack stearic bulk on the α-carbons which merely have hydrogen radicals thereon, thus rendering the phosphites susceptible to hydrolytic instability, and possibly volatile degradation products.

Accordingly, it would be desirable to provide phosphites which have few beta-hydrogens (preferably no beta-hydrogens) and have stearic bulk on the α -carbon.

SUMMARY OF THE INVENTION

The present invention provides organic phosphite esters which (a) have few hydrogens on the beta-carbons, and preferably no hydrogens on the beta-carbons, and (b) have stearic bulk on at least one alpha-carbon. The phosphites are suitable for use as thermal oxidative stabilizers in polymeric compositions.

DETAILED DESCRIPTION OF THE INVENTION

The phosphites include those of the general formula:

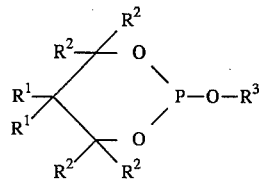

wherein each $R^2$ is independently selected from hydrogen and hydrocarbon radicals provided however that at least one $R^2$ is a hydrocarbon which provides stearic bulk to the α-carbon it is attached to, wherein the combined total number of beta-hydrogen on each $R^2$ radical is no greater than one, and preferably zero, wherein the $R^1$ and $R^2$ radicals have a combined total of carbon atoms of at least five; and wherein the $R^3$ is a hydrocarbon radical having at least six carbon atoms and may contain phosphite moieties.

Preferably the phosphite is obtained by the reaction of a neoglycol with $PCl_3$ in the absence of a catalyst, HCl acceptor and solvent to produce an intermediate product of the formula:

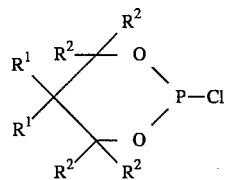

wherein $R^1$ and $R^2$ are defined above, followed by reaction with HO—$R^3$ wherein $R^3$ is defined above. Alternatively, other reaction processes and steps may be employed to yield the desired product. Transesterification processes such as those disclosed in Heckenbleikner et al., U.S. Pat. No. 3,056,823, which is incorporated herein by reference, may also be employed. The phosphites can be made, for instance, by reacting a diol of the formula

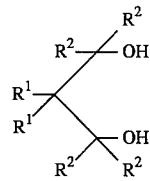

with triphenylphosphite by heating in the presence of an alkaline catalyst, e.g., an alkali metal, alkaline earth metal or metal alcoholate. The reaction proceeds essentially as a substitution reaction, with an aliphatic group replacing one or more aryl groups in the triaryl phosphites. The proportions of the aliphatic alcohol and triaryl phosphite are selected accordingly. Thus there is used 1 mole of aliphatic diol to replace 2 moles of aryl radicals from the original phosphite, with the liberation of 2 moles of phenol. Reaction temperatures may vary widely but in general are between about 120° and 150° C.

In practice, the dihydric alcohol, triphenyl phosphite ester and catalyst may be mixed together in any desired order, preferably before heating is started. The materials are then heated together, as, for example, under a reflux condenser, until the substitution of aliphatic for aryl components has reached the desired state. This can be determined by no further change in observable properties such as the boiling point of the mixture. The period of heating required is usually 2–5 hours. Heating is then discontinued. The phenol or other arylhydroxy compound liberated during the reaction as well as any unreacted aliphatic diol are distilled off in vacuum, and the resultant phosphite triester is recovered from the still residue and purified by conventional means.

$R^3$ may contain phosphite moieties.

As set out above, suitable diols are those of the formula

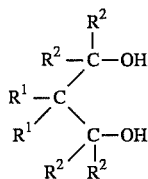

wherein each $R^1$ is preferably independently selected from the group consisting of alkyl radicals having from 1 to 10 carbon atoms, wherein each $R^2$ is independently selected from the group consisting of hydrogen and alkyl radicals having from 3 to 20 carbon atoms, provided that at least one $R^2$ is an alkyl radical having from 3 to 20 carbon atoms (preferably 4 to 6 carbon atoms). As described herein, the α-carbons are those directly attached to the oxygen atom and the β-carbons are those located two carbons from the oxygen atoms, thus the β-carbons are those attached to the α-carbons and the α-carbons are those attached to the oxygen atoms. For illustrative purposes, a phosphite of the formula

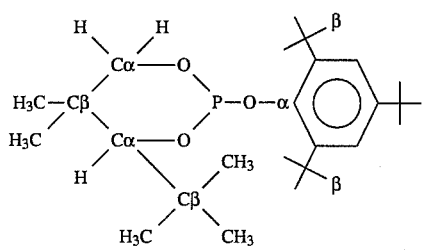

has no hydrogens attached to the beta carbons, and the corresponding diol

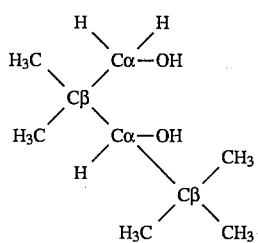

has no hydrogens attached to the beta-carbons. Preferably the phosphites of the present invention have no more than one hydrogen attached to each beta-carbon, preferably have no more than a total of two such beta-hydrogens for the entire phosphite, and more preferably have no more than one such beta-hydrogen, and most preferably have no hydrogens attached to the beta carbons. Neotype glycols utilizable in the invention having beta, beta dialkyl substitutions and having at least one $R^2$ being a hydrocarbon radical to provide the α-carbon with stearic bulk. Specific neo-glycols include those having no hydrogens attached to the beta carbons:

2,2-dimethyl-1-t-butyl-1,3 propane diol,
2,2-dimethyl-1,3-di-t-butyl propane diol,
2-ethyl-2-butyl-1-t-butyl-1,3 propane diol,
2-ethyl-2-butyl-1,3-di-t-butyl-1,3 propane diol,
2,2-dimethyl-1-t-butyl-1,3-propane diol,
2,2-diethyl-1-t-butyl-1,3-propane diol,
2,2-dipropyl-1-t-butyl-1,3-propane diol,
2,2,-dibutyl-1-t-butyl-1,3 propane diol,
2,2-diphentyl-1-t-butyl-1,3-propane diol,
2,2-dihexyl-1-t-butyl-1,3-propane diol,
2-methyl-2-ethyl-1-t-butyl-1,3-propane diol,
2-methyl-2-propyl-1-t-butyl-1,3-propane diol,
2-methyl-2-butyl-1-t-butyl-1,3-propane diol,
2-methyl-2-pentyl-1-t-butyl-1,3-propane diol,
2-methyl-2-hexyl-1-t-butyl-1,3-propane diol,
2-ethyl-2-propyl-1-t-butyl-1,3-propane diol,
2-ethyl-2-butyl-1-t-butyl-1,3-propane diol,
2-ethyl-2-pentyl-1-t-butyl-1,3-propane diol,
2-ethyl-2-hexyl-1-t-butyl-1,3-propane diol,
2-propyl-2-butyl-1-t-butyl-1,3-propane diol,
2-propyl-2-pentyl-1-t-butyl-1,3-propane diol,
2-propyl-2-hexyl-1-t-butyl-1,3-propane diol,
2-butyl-2-pentyl-1-t-butyl-1,3-propane diol,
2-butyl-2-hexyl-1-t-butyl-1,3-propane diol,
2-pentyl-2-hexyl-1-t-butyl-1,3-propane diol,
2,2-dimethyl-1-t-butyl-3-t-butyl-1,3-propane diol,
2,2-diethyl-1-t-butyl-3-t-butyl-1,3-propane diol,
2,2-dipropyl-1-t-butyl-3-t-butyl-1,3-propane diol,
2,2,-dibutyl-1-t-butyl-3-t-butyl-1,3 propane diol,
2,2-dipentyl-1-t-butyl-3-t-butyl-1,3-propane diol,
2,2-dihexyl-1-t-butyl-3-t-butyl-1,3-propane diol,
2-methyl-2-ethyl-1-t-butyl-3-t-butyl-1,3-propane diol,
2-methyl-2-propyl-1-t-butyl-3-t-butyl-1,3-propane diol,
2-methyl-2-butyl-1-t-butyl-3-t-butyl-1,3-propane diol,
2-methyl-2-pentyl- 1-t-butyl-3 -t-butyl-1,3 -propane diol,
2-methyl-2-hexyl-1-t-butyl-3-t-butyl-1,3-propane diol,
2-ethyl-2-propyl-1-t-butyl-3-t-butyl-1,3-propane diol,
2-ethyl-2-butyl-1-t-butyl-3-t-butyl-1,3-propane diol,
2-ethyl-2-pentyl-1-t-butyl-3-t-butyl-1,3-propane diol,
2-ethyl-2-hexyl-1-t-butyl-3-t-butyl-1,3-propane diol,
2-propyl-2-butyl-1-t-butyl-3-t-butyl-1,3-propane diol,
2-propyl-2 -pentyl - 1 -t-butyl - 3 -t-butyl-1,3 -propane diol,
2-propyl-2 -hexyl- 1-t-butyl-3 -t-butyl-1,3-propane diol,
2-butyl-2-pentyl-1-t-butyl-3-t-butyl-1,3-propane diol,
2-butyl-2-hexyl-1-t-butyl-3-t-butyl-1,3-propane diol,
2-pentyl-2-hexyl-1-t-butyl-3-t-butyl-1,3-propane diol As indicated, at least one $R^2$ is preferably a tertiary alkyl, and may be represented by the formula:

wherein each $R^4$ is independently selected from the group consisting of an alkyl radical having from 1 to 10 carbon atoms, preferably each $R^4$ is a methyl group.

Neodiols having one beta-hydrogen include those wherein at least one $R^2$ is of the formula:

where $R^4$ is as defined above. Specific neodiols having one beta-hydrogen include:
2,2-dimethyl-1-(2-propyl)-1,3-propane diol,
2,2-diethyl-1-(2-propyl)-1,3-propane diol,
2,2-dipropyl-1-(2-propyl)-1,3-propane diol,
2,2,-dibutyl-1-(2-propyl)-1,3 propane diol,
2,2-dipentyl-1-(2-propyl)-1,3-propane diol,
2,2-dihexyl-1-(2-propyl)-1,3-propane diol,
2-methyl-2-ethyl-1-(2-propyl)-1,3-propane diol,
2-methyl-2-propyl-1-(2-propyl)-1,3-propane diol,
2-methyl-2-butyl-1-(2-propyl)-1,3-propane diol,
2-methyl-2-pentyl-1-(2-propyl)-1,3-propane diol,
2-methyl-2-hexyl-1-(2-propyl)-1,3-propane diol,
2-ethyl-2-propyl-1-(2-propyl)-1,3-propane diol,
2-ethyl-2-butyl-1-(2-propyl)-1,3-propane diol,
2-ethyl-2-pentyl-1-(2-propyl)-1,3-propane diol,
2-ethyl-2-hexyl-1-(2-propyl)-1,3-propane diol,
2-propyl-2-butyl-1-(2-propyl)-1,3-propane diol,
2-propyl-2-pentyl-1-(2-propyl)-1,3-propane diol,
2-propyl-2-hexyl-1-(2-propyl)-1,3-propane diol,
2-butyl-2-pentyl-1-(2-propyl)-1,3-propane diol,
2-butyl-2-hexyl-(2-propyl)-1,3-propane diol,
2-pentyl-2-hexyl-(2-propyl)-1,3-propane diol
The moiety of the formula

may be another phosphite moiety or may be derived from an alcohol of the formula $$H{-}O{-}R^3$$

which includes alcohols of the formula

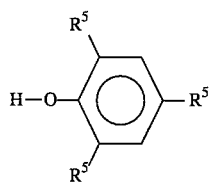

wherein each $R^5$ is independently selected form the group consisting of hydrogen and hydrocarbon radicals, preferably at least two of the $R^5$ groups are alkyl radicals having from one to ten carbon radicals, more preferably at least two of the $R^5$ groups are t-butyl groups, preferably the sum of carbon atoms in the $R^5$ groups is at least 6 and more preferably two $R^5$ groups adjacent the oxygen are each alkyl groups.

The phosphite of the present invention may be diphosphites where $R^3$ contains a phosphite moiety. Suitable diphosphites include those of the formula

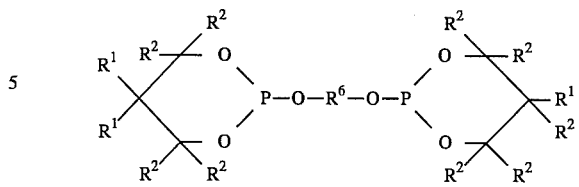

wherein $R^1$ and $R^2$ for each phosphite moiety are defined above, wherein $R^6$ is a divalent hydrocarbon radical preferably having few, more preferably zero hydrogens attached to the beta-carbon. The moiety —O—$R^6$—O— may be derived from a diol of the formula $$HO{-}R^6{-}OH$$

Suitably $R^6$ structures include

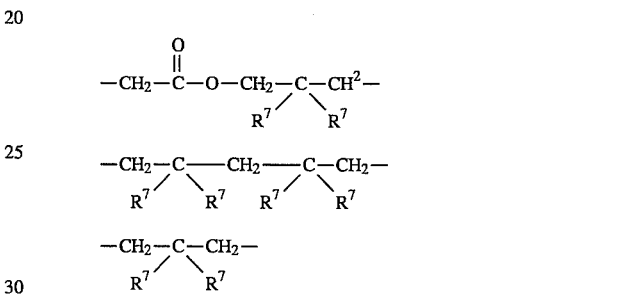

wherein each $R^7$ is independently selected from alkyl radicals having from 1 to 6 carbon atoms, and $R^8$ is a divalent hydrocarbon radical having from 1 to 20 carbon atoms, preferably 1 to 6 carbon atoms. Suitable phosphites include those of the following structures:

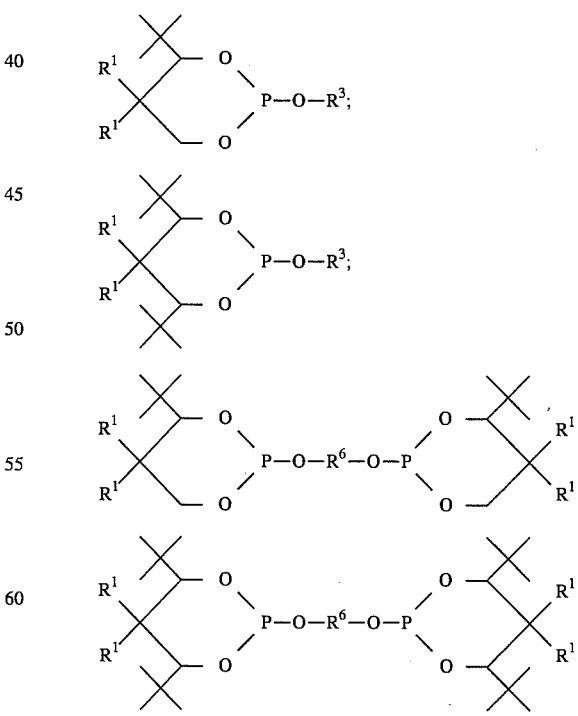

Preferably each $R^1$ is methyl.
Examples of specific structures include:

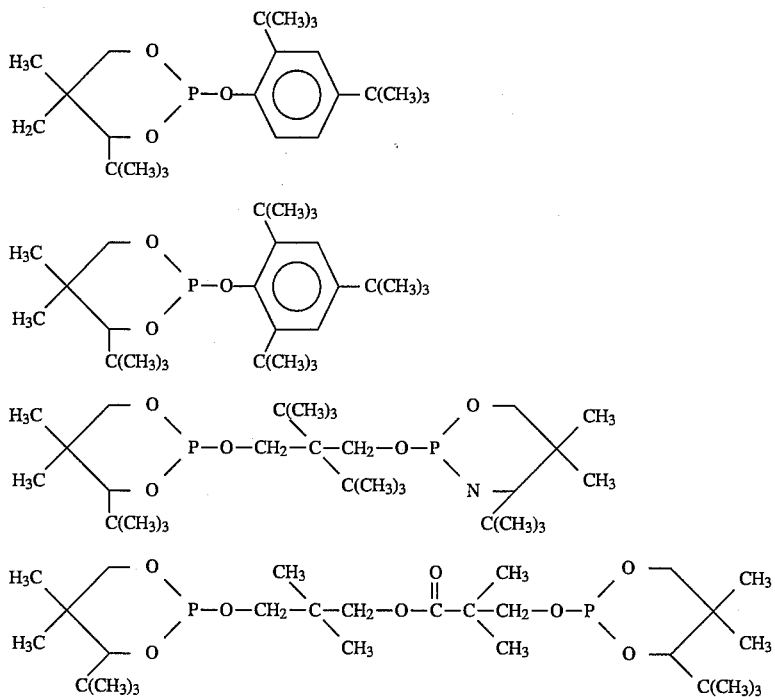

The phosphites are useful for stabilizing polymers from thermal oxidative degradation. Suitable polymeric compositions include polyolefins (polypropylene, polyethylene, polybutene, poly (2-methyl-pentene), polycarbonates, polyesters (PET, PBT, PCTG), polyamides polyurethanes, rubber modifiers, graft copolymers (MBS, ABS, MB, ASA) and polystyrenes.

The present invention also is a stabilized polymer composition which includes an effective amount of one or more of the phosphites described above. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxy, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/ isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/ EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/ butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; sytrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadienepolymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4 -dimethylol-cyclohexane-terephthalate, poly-2(2,2,4(4 -hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4,polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6 -di-tertbutyl-4-methylphenol, 2-tert-butyl-4,6-dimethylphenol, 2,6-di-tert-butyl-4-ethylphenol, 2,6 -di-tert-butyl-4-n-butylphenol, 2,6-di-tert-butyl-4-isobutylphenol, 2,6-dicyclopentyl-4-methylphenol, 2 -(alpha-methylcyclohexyl)-4,6 dimethylphenol, 2,6 -dioctadecyl-4-methylphenol, 2,4,6,-tricyclohexyphenol, 2,6-di-tert-butyl-4-methoxymethylphenol.

1.2 Alkylated hydroquinones, for example, 2,6 -di-tertbutyl-4-methoxyphenol, 2,5-di-tert-butylhydroquinone, 2,5-di-tert-amyl-hydroquinone, 2,6 -diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4' -thio-bis-(6-tert-butyl-2-methylphenol).

1.4 Alkylidene-bisphenols, for example, 2,2' -methylene-bis-(6-tert-butyl-4-methylphenol), 2,2' -methylene-bis-(6-tert-butyl-4-ethylphenol), 2,2' -methylene-bis-(4-methyl-6-(alphamethylcyclohexyl)phenol), 2,2'-methylene-bis-(4 -methyl-6-cyclohexylphenol), 2,2'-methylene-bis-(6 -nonyl-4-methylphenol), 2,2'-methylene-bis-(6-nonyl- 4-methylphenol), 2,2'-methylene-bis-(6 -(alpha-methylbenzyl)-4-nonylphenol), 2,2'-methylene-bis-(6 -(alpha,alpha-dimethylbenzyl)-4-nonyl-phenol). 2,2' -methylene-bis-(4,6-di-tert-butylphenol), 2,2' -ethylidene-bis-(6-tert-butyl-4-isobutylphenol), 4,4' -methylene-bis-(2,6-di-tert-butylphenol), 4,4' -methylene-bis-(6-tert-butyl-2-methylphenol), 1,1 -bis-(5-tert-butyl-4-hydroxy-2-methylphenol)butane. 2,6-di-(3-tert-butyl-5-methyl-2- hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'methylbenzyl)-6-tert-butyl-4-methylphenyl)terephthalate.

1.5 Benzyl compounds, for example, 1,3,5-tris-(3,5-di-tert-butyl-4-hydroxybenzyl)-2,4,6 -trimethylbenzene, bis-(3,5-di-tert-butyl-4-hydroxybenzyl)sulfide, isooctyl 3,5-di-tert-butyl- 4-hydroxybenzyl-mercapto-acetate, bis-(4-tert-butyl- 3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris-(3,5 -dicyclohexyl-4-hydroxybenzyl)isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4 -hydroxyanilino)-s-triazine, octyl-N-(3,5-di-tert-butyl-4-hydroxyphenyl)-carbamate.

1.7 Esters of beta-(3,5-di-tert-butyl-4 -hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethylisocyanurate, thiodiethyleneglycol, dihydroxyethyl oxalic acid diamide.

1.8 Esters of beta-(5-tert-butyl-4-hydroxy-3 -methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4 -hydroxyphenol)-propionic acid for example, N,N'-di-( 3,5-di-tert-butyl-4-hydroxyphenylpropionyl)hexamethylen-diamine, N,N'-di-(3,5-di-tert-butyl-4-hydroxyphenylpropionyl)trimethylenediamine, N,N'-di-(3, 5-di-tert-butyl-4-hydroxyphenylpropionyl)hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-, 5'(1,1,3,3-tetramethylbutyl)-,5-chloro-3',5' -di-tert-butyl-,5-chloro-3'tert-butyl-5'methyl-,3' sec-butyl-5'tert-butyl-,4'-octoxy,3',5'-di-tert-amyl- 3',5'-bis-(alpha, alpha-dimethylbenzyl)-derivatives.

2.2 2-Hydroxy-benzophenones, for example, the 4-hydroxy-4-methoxy-,4-octoxy,4-decyloxy-,4 -dodecyloxy-,4-benzyloxy,4,2',4'-trihydroxy- and 2'hydroxy-4,4'-dimethoxy derivative.

2.3 Esters of substituted and unsubstituted benzoic acids for example, phenyl salicylate, 4 -tert-butylphenyl-salicilate, octylphenyl salicylate, dibenzoylresorcinol, bis-(4-tert-butylbenzoyl)resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis(4-(1,1,1,3 -tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-1auroyl-5-hydroxy-pyrazole, optionally with additional ligands.

2.6 Sterically hindered amines, for example bis(2,2,6,6-tetramethylpiperidyl)-sebacate, bis-( 1,2,2,6,6-pentamethylpiperidyl)-sebacate, n-butyl- 3,5-di-tert-butyl-4-hydroxybenzyl malonic acid bis(1,2,2,6,6,-pentamethylpiperidyl)ester, condensation product of 1-hydroxyethyl-2,2,6,6 -tetramethyl-4-hydroxy-piperidine and succinic acid, condensation product of N,N'-(2,2,6,6 -tetramethylpiperidyl)-hexamethylendiamine and 4 -tert-octylamino-2,6-dichloro-1,3,5-s-triazine, tris-( 2,2,6,6-tetramethylpiperidyl)-nitrilotriacetate, tetrakis-(2,2,6,6-tetramethyl-4-piperidyl)-1,2,3,4 -butane-tetra-carbonic acid, 1,1'-(1,2 -ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-( 3,5-di-tert-butyl-4-hydroxy hydrocinnamoyloxy)piperdine; and N-(1-hydroxy-2,2,6,6-tetramethylpiperidin-4-71)-epsiloncaprolactam.

2.7 Oxalic acid diamides, for examples, 4,4' -dioctyloxyoxanilide, 2,2'-di-octyloxy-5',5'-di-tert-butyloxanilide, 2,2'-di-dodecyloxy-5',5'-di-tert-butyl-oxanilide, 2-ethoxy-2'-ethyl-oxanilide, N,N'-bis(3-dimethylaminopropyl)-oxalamide, 2-ethoxy- 5-tert-butyl-2'-ethyloxanilide and its mixture with 2-ethoxy-2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2, 4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tertbutylphenyl)- 4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate; ethyl- 3-(N,N-dibenzylaminoxy)propanonoate; 1,6 -hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)propanoate; 3-(N,N-dibenzylaminoxy)propanoic acid potassium salt; and 1,6-hexamethylene bis(3 -(N-allyl-N-dodecyl aminoxy)propanoate).

11. Other additives, for example, plasticizers, lubricants, emulsifiers, pigments, optical brighteners, flameproofing agents, anti-static agents, blowing agents and thiosynergists such as dilaurythiodipropionateordistearylthiodipropionate.

Polymeric particles may be coated with the present phosphites alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by supported Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti or Zr.

Consistent with the invention, the phosphites of the invention may be added to the polymer at any time prior to or during fabrication into articles and may be combined with the polymer by any of a variety of means known in the art, such as by preblending or by being fed directly into fabrication equipment.

The polypropylene compositions may include residual catalyst such as Ziegler catalysts which may be carried on a support (i.e. $TiCl_3$ on $MgCl_2$). Other stabilizers may also be incorporated in the compositions.

EXAMPLES

The following examples illustrate the thermal oxidative stabilizing ability of the phosphites of the present invention in polypropylene. The formulation in examples A–B and 1,2 where polypropylene containing 600 parts per million (ppm) of phosphite, 500 ppm phenolic antioxidant (Irganox 1010 available from Ciba-Giegy), 500 ppm calcium stearate.

Example A was a commercially available phosphite.

In Examples A and 1–2 the YI value is the yellowness index for the polypropylene compositions after the 5th extrusion pass, and the delta YI is the change in the yellowness index from the 1st extrusion pass to the 5th extrusion pass; the MF is the melt flow index at 230° F. after the 5th extrusion pass, and the delta MF is the change in the yellowness index from one 1st extrusion pass to the 5th extrusion pass. Extrusion of the formations is as follows: Equipment: 1" Killion extruder with two stage screw (3:1 compression ratio) and a Maddox mixing element at 2:1 ratio, and Screw RPM at 100, back pressure at 1000 PSI that was established on Blend #1 during start-up and purge cycle. The ingredients were blended using Turbula Blender for 30 minutes. Liquid Additives were weighed into small amount of resin and then blended into approximately 1 pint of resin using Waring Blender. This blend of additive and resin then added to balance of resin and placed into Turbula blender for 30 minutes. Temperature profile of extruder: Rear: 200° C. Middle: 240° C., Front: 258° C., Die: 260° C. Actual Stock Temperature= 262° C. HS is hydrolytic stability of the phosphite composition in polymer determined by testing at 60° C./75% relative humidity in days to loss of 50% of the phosphite; UV is yellowing upon exposure to ultraviolet light with "P" indicating that it did not yellow and with "F" indicating that it yellowed. Hydrolytic stability requires bulk on the x carbon and requires a minimum of B hydrocarbons. Examples A, B and C are comparative examples. Examples 1–7 illustrate the present invention.

| Ex. | Phosphate | YI/ Delta YI | MF/ Delta MF | HS | UV |
| --- | --- | --- | --- | --- | --- |
| A | I168 | 5.87/2.91 | 11.49/5.54 | — | — |
| 1 | P-1 | 4.00/2.48 | 6.0/1.25 | 64 | P |
| 2 | P-2 | 6.04/2.97 | 6.0/1.36 | 54 | P |
| 3 | P-3 | — | — | 22 | F |
| 4 | P-4 | — | — | 4 | P |
| 5 | P-5 | — | — | 15 | F |
| 6 | P-3 | — | — | 22 | F |
| 7 | P-6 | — | — | 37 | P |
| B | P-7 | — | — | <2 | P |
| C | P-8 | — | — | 12 | F |

Note the improved hydrolytic stability of P-4 over P- and of P-3 over P-8.

I168 is a phosphite of the formula tri(2,4-di-t-butyl phenyl) phosphite.

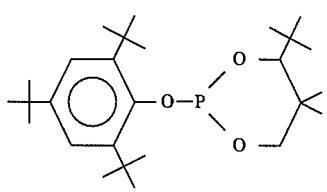

P-1

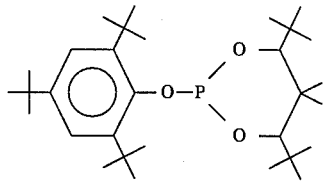

P-2

-continued

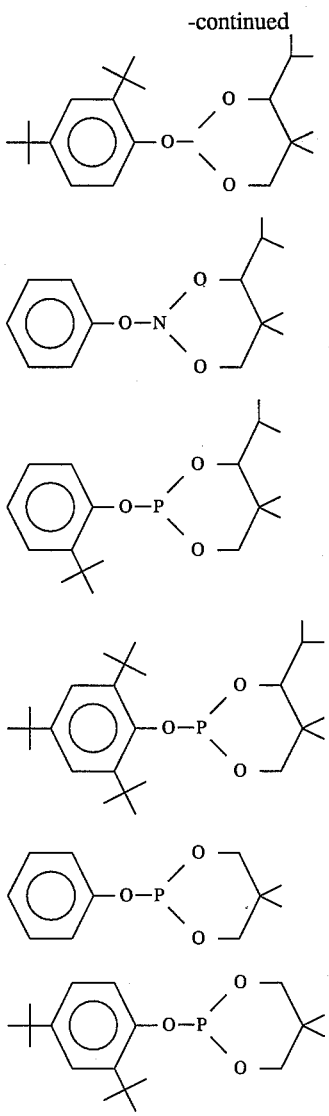

I claim:
1. A phosphite of the formula:

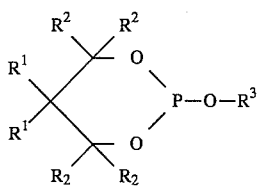

wherein each $R^1$ is independently selected from the group consisting of alkyl radicals having from 1 to 10 carbon atoms, each $R^2$ being independently selected from the group consisting of hydrogen and alkyl radicals having from 3 to 20 carbon atoms provided that at least one $R^2$ is an alkyl radical, $R^3$ being a hydrocarbon radical having at least 6 carbon atoms, and said phosphite having no hydrogen atoms directly attached to a beta carbon atom relative to the oxygen attached to the phosphorous atom.

2. The phosphite of claim 1 wherein the $R^1$ and $R^2$ radicals have a combined total of carbon atoms of at least 5.

3. The phosphite of claim 1 wherein said phosphite is selected from the group consisting of:

P-3

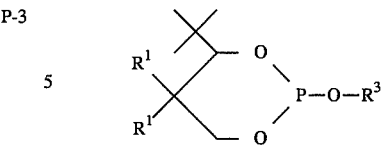

and

P-4

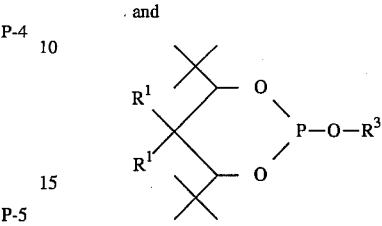

P-5 wherein $R^3$ is of the formula:

P-6

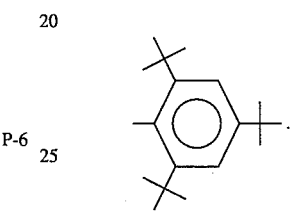

4. The phosphite of claim 3 wherein each $R^1$ is methyl.
5. A phosphite selected from the group consisting of phosphites of the formulas:

P-7

P-8

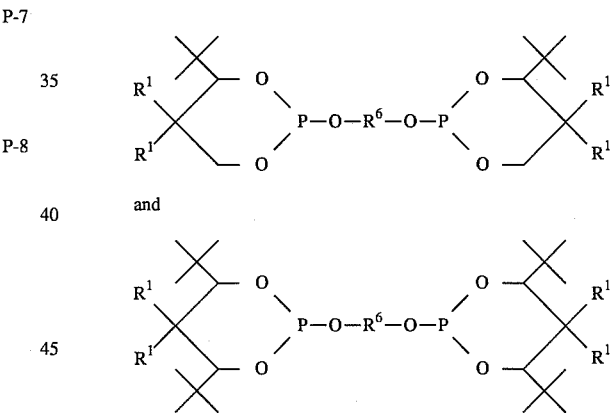

wherein each $R^1$ is independently selected from the group consisting of alkyl radicals having from 1 to 10 carbon atoms, each $R^6$ is a divalent radical selected from the group consisting of

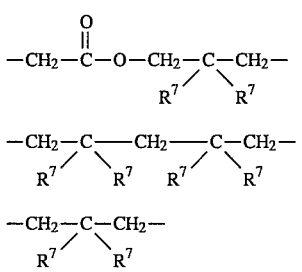

wherein each $R^7$ is individually selected from alkyl radicals having from 1 to 6 carbon atoms, said phosphite having no hydrogen atom directly attached to a beta carbon atom relative to the oxygen attached to the phosphorous atom.

6. A polymeric composition comprising (a) a polymer selected from the group consisting of polyolefins, polyesters, polycarbonates, rubber modified graft copolymers, polyamides, polyetherimides, polyphenylene ethers, polyvinylhalides, polystyrenes, and polyurethanes, and (b) a phosphite as claimed in claim 5.

* * * * *